United States Patent [19]
Franconi et al.

[11] Patent Number: 5,099,756
[45] Date of Patent: Mar. 31, 1992

[54] RADIO FREQUENCY THERMOTHERAPY

[75] Inventors: Cafiero Franconi; Carlo A. Tiberio, both of Rome, Italy; Harry H. LeVeen, 321 Confederate Cir., Charleston, S.C. 29407

[73] Assignee: Harry H. LeVeen, Charleston, S.C.

[21] Appl. No.: 360,244

[22] Filed: Jun. 1, 1989

[51] Int. Cl.$^5$ .............................................. A61N 2/04
[52] U.S. Cl. ...................................... 600/10; 600/13; 600/14; 128/804; 336/229; 219/10.79
[58] Field of Search .................. 600/9, 10, 12, 13, 14; 128/804; 336/229; 219/10.79

[56] References Cited

U.S. PATENT DOCUMENTS

| 3,890,953 | 6/1975 | Kraus et al. | 600/14 |
| 4,325,361 | 4/1982 | Harrison | 600/10 |
| 4,402,309 | 9/1983 | Harrison | 600/10 |
| 4,674,481 | 6/1987 | Boddie, Jr. et al. | 600/10 |

FOREIGN PATENT DOCUMENTS

| 3333288 | 4/1985 | Fed. Rep. of Germany | 600/13 |
| 3721864 | 1/1989 | Fed. Rep. of Germany | 600/13 |
| 1007681 | 3/1983 | U.S.S.R. | 600/13 |

OTHER PUBLICATIONS

Y. Kotsuka et al., "Ferrite Applicator and Implant Material for Local Hyperthermia of Induction Heating", in: T. Sugahara and M. Saito (eds.), Proc. Symp. on Hyperthermic Oncology, vol. 1, pp. 843-844, Taylor and Francis, Bristol, 1989.

Y. Saitoh et al., "A Re-Entrant Resonant Cavity Applicator for Deep and Concentrated Hyperthermia", in: T. Sugahara and M. Saito (eds.), Proc. Symp. on Hyperthermic Oncology, vol. 1, pp. 837-838, Taylor and Francis, Bristol, 1989.

Primary Examiner—Lee S. Cohen
Attorney, Agent, or Firm—Gipple & Hale

[57] ABSTRACT

Apparatus for treating neoplasms in humans and animals comprising a hollow toroidal applicator which resonates at a specific radiofrequency, and which possess electrically conductive walls on which radial radiofrequency currents flow and generate a high density of uninterrupted magnetic flux within the hollow body. A rotatable antenna connected to a source of radiofrequency power is mounted inside the applicator body to couple with the electromagnetic field of the applicator. The body part to be treated is interposed through side apertures or through the space created by removing a segment of the toroid which can have orifices of predetermined cross sectional areas across which a tubular zone of high magnetic flux travels through the interposed tumor and normal tissue to induce more heat in the interposed tumor tissue than in the interposed normal tissue.

15 Claims, 12 Drawing Sheets

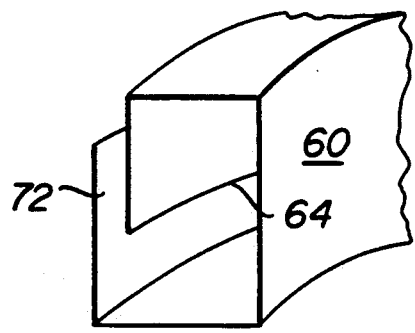
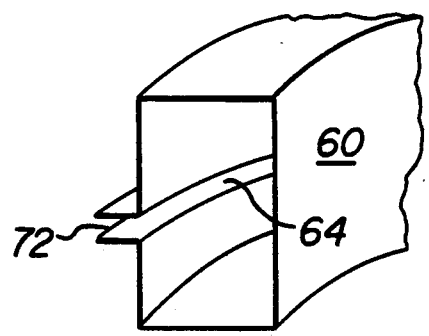
FIG. 3  FIG. 4
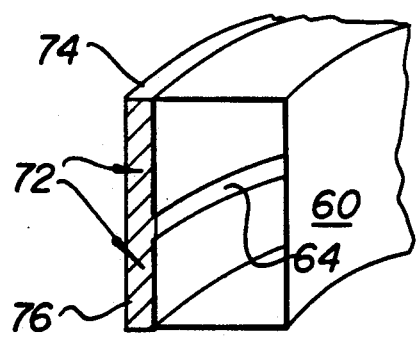
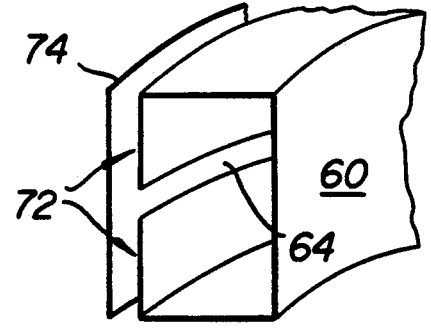
FIG. 5  FIG. 6

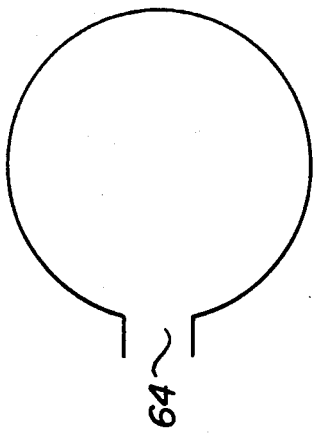
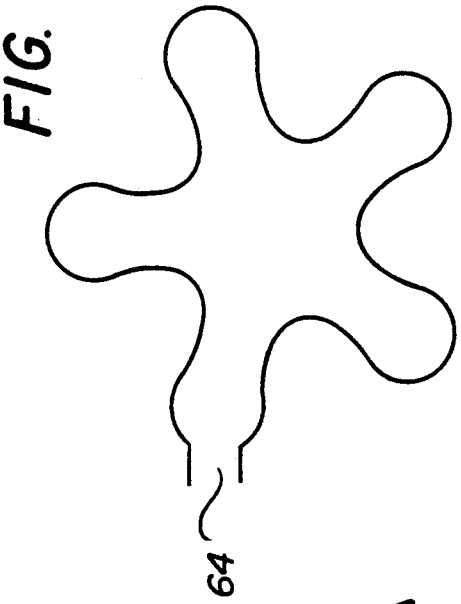
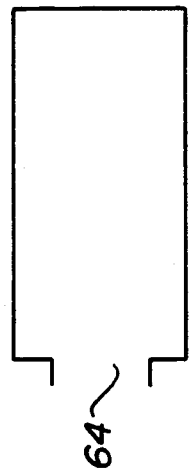
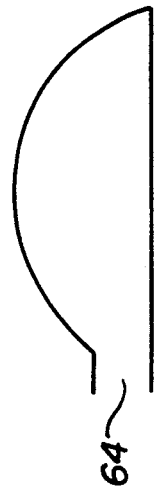
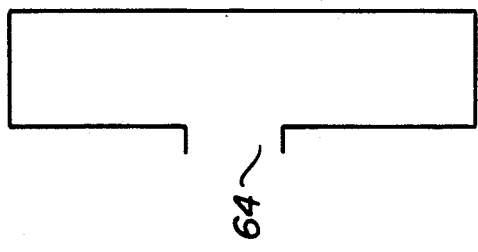
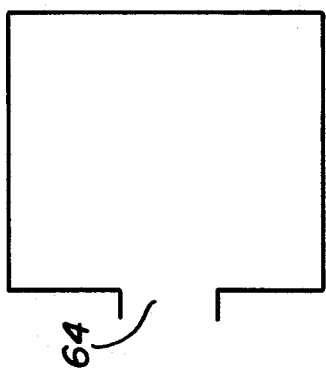
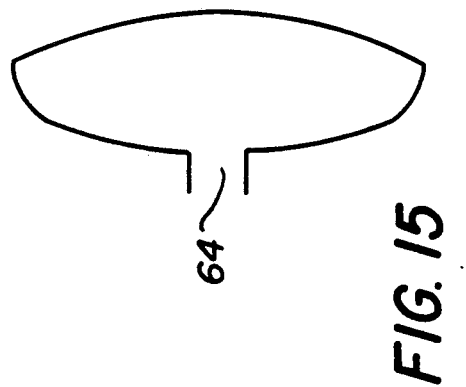

RADIO FREQUENCY THERMOTHERAPY

BACKGROUND OF INVENTION

Heating of cancer tissue has been found to be beneficial in several ways. First, the heat may directly kill tumor cells, especially hypoxic cells in the center of the tumor. Secondly, the heated cells will liberate tumor antigens and thus sensitize the immune system to specific cancer tumor antigens, which helps to control the growth of cancer tissue. Thirdly, heat destroys the fragile neovasculature which develops in the tumor. These listed benefits are not the only beneficial effects of heat in cancer therapy since heat intensifies the killing effect of ionizing radiation or chemotherapy or both. As an example, the killing effect of chemotherapeutic agents is often enhanced in excess of more than two orders of magnitude. For these reasons, heat must be included in the therapeutic considerations for the treatment of all human cancers along with radiation and chemotherapy.

This invention relates to the treatment of tumors in animal hosts, such as human beings, and in particular provides a technique for destroying the tumor without injury to adjacent normal tissue. The tumors can be benign or malignant and include carcinomas, sarcomas, and avascular lesions.

It is an important aspect of this invention to provide an apparatus applicable to the treatment of tumors under a wide variety of conditions which can be utilized with a minimum, and preferably an absence, of surgery.

It has been noted that tumors can be affected by hyperthermia (Brit. of Cancer 25:771, 1971; Cancer Research 32:1916, 1972) and this observation was coupled with the notation that the tumors were heat sensitive. Experiments with external surface heating do not produce deep heating and in some cases, using hyperthermia, the whole animal was heated as much as the tumor. Others have felt that a slight raise in temperature produced by metabolic changes interfered with cell growth (Europe. J. Cancer 9:103, 1973). Still others have heated tumors a few degrees by diathermy and observed that the effect on the tumor was inhibitory but not destructive (Zeit. fur Naturforschung 8, 6:359, 1971). There is still some disagreement in the role heat may play in the treatment of cancer (The Lancet, May 3, 1975;1027).

Anatomical studies suggest the blood flow through carcinomas and other neoplasms is sluggish (Acta Pathalogica Microbiological Scand., 22:625, 1945; Advances in Biology of the Skin, 21:123, 1961). Furthermore, tumors possess an angio-genetic factor which initiates the formation of new blood vessels. The blood vessels which are stimulated to grow are capillaries, which because of their small diameter offer great resistance to blood flow. These tumor initiated capillaries make connections with the normal capillaries on the periphery of the tumor and form tortuous haphazard pathways before emptying into some small veins at the periphery of the tumor. Frequently, there is marked venous obstruction within the tumor caused by compression of the peripheral veins due to enlargement of the tumor and growth of tumor cells into the blood vessels obstructing them.

Anatomical studies also demonstrate the presence of arterio-venous fistulae at the periphery of tumors which can cause the tumors to appear vascular and on angiography cause the rapid appearance of contrast media. However, these fistulae at the periphery of the tumor tend to create a low resistance pathway at the surface of the tumor which lowers the arterial pressure and diverts blood from entering the tumor.

Although anatomical studies suggest that tumor blood flow is diminished and slow, angiographic studies have functionally confirmed that blood flow through a tumor is actually sluggish. Residual contrast medium remains in the tumor after it has been swept out of the adjacent normal tissue by normal blood flow. This remaining residual contrast medium has been called a "Tumor Stain". The tumors which have been most studied radiographically have been brain tumors and kidney tumors.

A sluggish flow has been confirmed by the indicator dilution technique which measures the actual flow of blood through normal tissue and through tumors. The indicator dilution technique is more reliable than the visual method as seen on angiography. Such studies were done in vivo using x-ray contrast medium dilution and in vivo on excised specimens. In the excised specimens, blood flow was measured by an indicator dilution technique before using radio-iodinated serum albumin. The albumin molecule was tagged with $I_{131}$ and the isotope dilution was measured in the tumor and in normal tissue by a collimated scintillation counter. These studies indicated that the magnitude of flow through the adjacent normal tissue is such that the tumor tissue is differentially heated when the area of body containing the tumor is treated by diathermy.

It is known that tumors are usually destroyed by a quantum of heat which would be delivered by a temperature of 45° C. over a period of three hours. Exposure at higher temperature requires less time. At 50° C., the time is reduced to a mere ten minutes. Such temperatures, of course, also destroy or severely damage normal tissue and the present invention utilizes one of the Applicant's prior discoveries. When a portion of the body is heated, for example, by applied radio frequency electromagnetic radiation, the tumor is heated differentially to a greater extent, such that the temperature of the normal tissue adjacent the tumor can be kept below 40° C.

This effect is caused primarily by the normal blood flow in the adjacent normal, non-cancerous tissue, because the temperature at which tissue is heated is a function of the blood supply to the tissue. Although the blood itself is heated, it serves as a heat exchanger to carry heat away from the tissue being heated. Tissues which are poorly perfused with blood such as cancerous tissue become heated more rapidly and to a higher temperature than tissues which have a normal rate of blood flow. As pointed out above, cancerous and other malignant and benign growths develop outside a preformed blood distribution network and derive their blood supply from the periphery of the tumor where it meets the adjacent normal blood supply. As a consequence, the slow rate of volume and blood flow through the tumor provides a lesser cooling rate in the tumor than the flow of blood through the normal tissues adjacent to the tumor.

Such treatment of cancer has finally been disclosed in U.S. Pat. No. Re 32,066 dated Jan. 21, 1986 and, the references cited therein.

The apparatus for heating tumors in the '066 patent employed an amplifier which amplified the output of a crystal oscillating at 13.56 or 27.12 megaHertz. Crystal oscillators were used to insure that the generated frequencies were within the band allocated to medical use, otherwise it would be necessary to place the patient together with the R. F. generator into a Faraday cage to shield against leakage into the environment. However, studies on patients during RF treatment disclosed that the amount of RF in the immediate environment was usually greater than permitted by OSHA standards.

U.S. Pat. No. 4,285,346 describes an impedance matching unit which may be used between a radio frequency generator or source and a pair of electrodes placed adjacent a body. This reference also describes arrangements using a plurality of pairs of electrodes, pairs of which may be rendered separately inoperative by grounding of the transmission cable extending from the matching unit to a pair of electrodes.

U.S. Pat. No. 4,356,458 describes an apparatus for automatically adjusting the impedance of an electrical circuit connected to a radio frequency source so as to maintain the impedance of the circuit at a substantially constant value to permit the maximum transfer of energy to the load forming part of the circuit, and relates particularly to apparatus for use with, the short wave diathermy apparatus described in the above mentioned '346 patent.

U.S. Pat. No. 4,230,129 relates to a "C" shaped apparatus with electromagnetic energy applicator plates. The exact position and configuration of the tumor is plotted in terms of rectangular coordinates and the radio frequency equipment can then be directed or focused on the tumor location in order to avoid excessive heating or thermal damage to the surrounding tissue. The applicator plates or discs are moved in an orbital manner such that the tumor always lies on the axis between the applicator plates and the radio frequency energy is concentrated therein. Because of the orbital movement of the apparatus, the energy is not continuously being applied to a confined area, i.e., to immediately surrounding tissue, but rather is applied over a comparatively large surface area so as not to affect the surrounding tissue adversely.

Yet, as beneficial as heat has proven to be, it is often difficult or impossible to raise the tumor temperature sufficiently to produce the maximum tumor benefit without burning the skin or injuring adjacent organs and causing serious discomfort to the patient. In addition to these serious disadvantages to RF heating, the apparatus is expensive and remains ineffective for heating tumors deep in the body. For these reasons, an inexpensive method to introduce heat and localize it to a specific volume has presented a heretofore insoluble problem. If the heating is done by extremely short wavelengths, such as those in the microwave range (waves with a frequency in the region of 1,000 megaHertz) the absorption of energy in the superficial tissue is so great that the amount of energy reaching a deep-seated tumor will be insufficiently low. However, microwaves can be easily focused to direct them to the site of the tumor, while longer wavelengths, such as those in the range of 13.36 or 27.12 megaHertz, are of such length that they cannot easily be focused on target volumes as small as solid tumors. Yet, the absorption of these waves is far less and would be more useful if a method could be found to contain and direct their energy to a specific target.

Moreover, the lower the RF frequency, the larger the contribution of the quasi-static current term with respect to the radiation term in the deposited energy in lost tissue. Low frequency RF currents do not present any problem of penetration, therefore, it would be useful if a method was devised to direct and confine low frequency energy in such a way that a flux tube of high density energy could be confined to a circumscribed volume of tissue.

The specific absorption rate (SAR) of electromagnetic energy in a conductive tissue is proportional to $\sigma E^2$ where $\sigma$ is the local conductivity and E is the intensity of the local electric field in the tissue. If we limit our considerations to EM fields and associated currents in the RF range, the local E field (electric) may be made flowing into the body from para-corporal electrodes sometimes called the capacitive or dielectric heating method since the body can be considered a lossy dielectric between two capacitors). However, the E field may be indirectly created in the tissues by a magnetic coupling of the applicator to tissue through the H field (magnetic) generated by an inductive applicator sometimes called inductive heating because an electric field is induced in conductive tissue). In the capacitive method, the E fields from the electrodes present a forceful component perpendicular to the fatty subcutaneous tissue, thus heating the highly resistive fat with respect to the deeper (muscle) layer beneath the fat. If the inductive method is used instead of the capacitive method, the induced E fields and associated eddy currents are flowing parallel to the fat-muscle interface which minimizes heating of the non-conductive fat layer and allows for passage of considerably more energy to the deeper muscle or tumor tissue. The inductive method makes it possible to treat obese patients who cannot be treated by the capacitive method. The inductive heat method also allows for greater heat to be developed in tumors which are surrounded by tissue of high impedance. For example, cancers of the lung have a much lower impedance than the surrounding air containing lung which, because of its air content, presents a high impedance. Inductive heating will heat the high impedance lung tissue less and the conductive cancer tissue will receive more heat. A similar situation is encountered in abdominal cancers where the cancer, having a relatively low impedance, is surrounded by loops of gas filled bowel whose impedance is high due to their gas content. Thus, inductive heating allows the energy to be deposited in the more conductive cancerous tissue.

Inductive RF heating devices have taken the shape of coils with the coil design derived mainly from inductive diathermy practice. (See Lehman, J. F. "Therapeutic Heat and Cold", Williams & Wilkins, Baltimore, 1982; Oleson, J., IEEE Trans. Biomed Eng. Vol. BME-31, pp, 91-97; 1984). The described practice for external coil applicators is with the coil plane parallel or perpendicular to the body surface which changes the direction of the H field with respect to the body surface. EM theory teaches us that an H field always induces an E field and associated RF current loops always lie in planes perpendicular to the H field lines of force, and therefore parallel to the RF currents flowing in the metal coil. The heat deposition with these current carrying coils results in an intense gradient towards the loop center where no heat is deposited. A typical coil H field distribution in a cross section of a coil much larger than the tumor mass would produce little RF power deposition in the tumor and the heating would be maximum only near the inner coil surface and the induced E field would rapidly decrease to zero at the coil center. Improved results are expected by the use of low inductance cylindrical RF coils which generate a more uniform cross sectional field distribution than single turn coils. Nonetheless, the results obtained with both the cylindrical RF single turn coils lying parallel to the body surface load (Kato,H. J.Med.Sci. 7:35–46; 1983) and with the cylindrical coil RF single turn coil, coaxially loaded (Elliot,RS et al IEEE Trans.Biomed-.Eng.BME-29:61–64, 1982) displays a high degree of non-uniformity in the distribution of the H field on cross section. A further disadvantage of the coil design is that the magnetic dipole flux lines are not contained but are rather spread all around the open space which results in a dramatic decrease of RF energy density immediately outside the coil's cylindrical body. This puts a great deal of RF energy into the ambient environment and would expose the operators of the equipment to a dose of radio frequency beyond that allowed by OSHA standards and the standards of other countries. Therefore, the patient must be put in a Faraday cage to safeguard the operator. We have verified in the laboratory the low RF energy effectiveness of coil applicators when coupled in a perpendicular coil to body configuration. (IEEE Trans.-Micr.Theory and Tech.MTT-34:612–619; 1986). In addition, the patients are also exposed to unnecessarily high stray H fields which were not heating the tumor.

It may be concluded that previous coil design applicators are unsuitable for generating high density uniform magnetic fields in a circumscribed cross section which could be usefully directed and localized to a malignant tumor mass since the heating pattern cannot be controlled for safe and effective cancer therapy.

SUMMARY OF INVENTION

This invention relates to the treatment of tumors in animal hosts, such as human beings, and in particular provides an apparatus and technique for destroying the tumor without injury to adjacent normal tissue. The tumors can be either benign or malignant and include carcinomas, sarcomas, cysts, and avascular lesions. The present invention provides an apparatus applicable to the treatment of tumors under a wide variety of conditions and can be utilized with a minimum, and preferably an absence, of surgery.

The invention provides a method and an applicator for safe and confined heating of a malignant tumor at therapeutic temperatures. This is accomplished by directing the output of an RF generator (a Colpits type of RF generator is most satisfactory) via coaxial cable to an applicator, based on a toroidal resonator, which confines the RF magnetic field inside a duct formed by their donut shaped conductive walls. At low RF frequencies, the toroidal resonator consists simply of a multi-turn winding inductor in a toroidal shape. It may be tuned to resonance by a variable capacitor properly connected such as at the winding's terminals. At higher RF frequencies, the toroidal resonator consists of a distributed radial transmission line shorted at one peripheral end and tuned to resonance along the other peripheral end by a uniformly distributed capacitance. In order to create a therapeutic field, the resonators are interrupted, partially or totally, by cutting away suitable apertures to form an Open Mode Toroidal Resonator (OMTR).This allows either all or part of the flux tube to be coupled to an exposed part of the body. Heating according to the present technique includes the selection of an OMTR pathway, the shape and location of the apertures in relation to the part of the body being heated. This ensures that the part of the body to be heated is exposed to a well confined therapeutic field of high density which can be collimated to direct the H field through the tumor mass. The collimated H field generates hyperthermic temperatures substantially confined to within the tumor mass.

It is a further object of this invention to impart motion to the OMTR while the tumor is being heated. The generated H field can then be distributed over a wide area of skin surface while simultaneously keeping the tumor mass within the focus of the collimated beam. Such motion allows the generation of heat to be intermittent on the skin and other tissue encountered in the entrance portal of the beam, but assures constant heating of the tumor mass. A second object of the motion is to mold the shape of the density of the H beam so that the summated total energy received will have proper intensity in a chosen region. For instance, a circular motion could be chosen so that the vascular rind of the tumor received a greater quantity of heat that the avascular center of the tumor. Therefore, the OMTR will have a mechanical means to scan, rotate, and otherwise change position of the OMTR during the treatment session.

It is also the additional object of the invention to provide a method and a complex apparatus, including an OMTR and an auxiliary RF circuitry, for further enhancement of localized heating of a deep tumor mass, in conditions of improved effectiveness and safety. In this configuration, an OMTR device is generating heating RF in the body part to be treated while an auxiliary RF field generated by an auxiliary apparatus is superimposed on the primary RF field. Such an arrangement will give rise to a confined enhanced heating while the RF generators are operated individually at reduced RF power. The heating may be still further enhanced by the constructive interference effect, if phase coherent RF sources are provided for both the OMTR and the auxiliary RF fields and their relative phase, amplitude, and patterns over the target volume, are controlled. In a versatile version, all of the heating devices are energized by independent but coherent RF sources. In simpler dedicated applicators, the auxiliary circuits could be energized by suitable EM coupling to the primary OMTR power source or vice versa.

One object of the present invention is an OMTR device derived from a toroidal resonator. The conductive walls are totally interrupted by cutting away a radial segment enabling the OMTR device to present two terminal cross sectional apertures. The total field emerging from one cross section is due to enter uninterrupted the other cross section across the gap created by the removal of a segment. The portion of the body to be heated is placed in the air gap and surrounded either totally or partially by the H field created by the OMTR.

Another object of the present invention is an OMTR device with a single side aperture in the conductive wall of the toroidal resonator. The body part to be treated is placed over the aperture and may protrude into it. In this manner a portion of the uninterrupted magnetic field emerges sideways and penetrates that portion of the body exposed to the aperture generating localized superficial heating. This scheme may be used to treat superficial tumors such as squamous carcinoma of the skin.

A further object of the present invention is an OMTR device within which a pair of side apertures are made in the conductive wall without totally interrupting it. In this configuration the body part (e.g., an arm) to be treated is placed so that it enters the hollow flux guide on one side and exits the other side. In this situation the part to be treated traverses the hollow guide.

It is a primary object of the invention to create different shaped aperture segments for the OMTR, each resonant at the same frequency of the OMTR body, so that the H field may be shaped as it exits from the aperture. This creates different types of heating patterns with different configurations. These can be combined with the motion of the OMTR to further shape the configuration, size and density of the H field to the requirements of the tumor. These aperture segments may present different cross section shapes at its ends and be properly tuned and fitted to any cross section of the OMTR body in order to give the OMTR preferred aperture shapes. The OMTR device in itself may have multiple elements to allow for changes in size and shape by assembling different OMTR segments, all of which resonate at the same frequency and can be joined by mechanical means. There can be joints capable of being rotated or bent, making the OMTR device very flexible with respect to size and configuration.

Another object of the invention is to provide an RF matching circuit, easy to adjust during treatment. This is accomplished by terminating the RF feeding cable to a coupling loop inserted into the hollow interior of the OMTR through a small aperture in the side wall. Provision is made for rotating the loop antenna to adjust its magnetic coupling to the OMTR, thus providing a smooth matching of the OMTR to the power source.

By sealing the gap in the walls of the OMTR, the OMTR will be a suitable conduit for refrigerated air. It can be used to cool the inner sides of the resonator and to blow refrigerated air onto the surface of the skin being heated by RF currents. This cooling prevents skin burns; one of the major hazards of radio frequency thermotherapy.

The invention overcomes the previously noted problems with radio frequency applicators used in localized hyperthermia. The applicator acts as a flux guide and creates a through and through cylinder of high magnetic flux which is caused to flow through a selected area of the body thereby inducing therapeutic heat. The OMTR applicator consists of a hollow toroidal resonator with conductive sides usually of copper. In the high frequency version, one conductive side is interrupted by a circumferential slot (gap) in the metal; the edges of which act as a distributed capacitance connected to a radial signal turn coil. In practice, this slot is usually filled with a plastic or other dielectric so that the refrigerated air may be passed through the hollow core. This creates an inductance and a capacitance. The value of the former is changed by changing the cross-sectional size and the radii of the OMTR. The value of the latter may be adjusted by adding further distributed or lumped capacitors. By choosing these values correctly, the resonant frequency of the toroid can be set at any value down to 27.12 MegaHertz and below. Radio frequency (RF) waves are transported through the toroid and refrigerated air is forced through the toroid to prevent overheating of the patient's skin and the walls of the resonator applicator. A segment of the toroid is removed and the part of the body to be heated is placed within the created aperture of the resonator. The completion of the magnetic circuit is accomplished in the body part, thus creating a tube of high magnetic flux density through the body part. Heat is created in the body by producing eddy currents in conductive tissue. In addition, suitable mechanical scans of the applicator spread the deposited electromagnetic energy over a wide skin area while continuously maintaining a high average flux density in the tumor.

These and other objects and advantages of the present inventive apparatus will become more readily apparent in the following detailed description thereof, together with the appended drawings.

It is a general object of the invention to provide a method and an apparatus for the enhancement of heating of neoplasms with respect to area of the tumor bed by depositing suitable ferrites and other material in the cancer tissue preferably by injection through a needle. Ferrites are chosen which absorb a high percentage of the RF magnetic field which reaches the tumor from the OMTR applicator. This material can take any form that of macroscopic or microscopic particles which are suspended in bio-compatible fluid carrier. The energy dissipated by eddy currents and/or hysteresis in the ferromagnetic particles is converted directly into heat, and the implanted material acts as a useful secondary heat source localized within the tumor mass itself.

A further application of the OMTR phenomenology, which also falls within the scope of this invention, is the following. A single OMTR segment the length of which is only a small portion of the length of the OMTR flux lines may be employed for heating superficial and subcutaneous tumors with advantage over simple superficial coil (pancake-like coils) heatings. In fact, the smaller RF voltage across the radial current lines of the OMTR generates a corresponding lower E field intensity and therefore smaller subcutaneous fat heating. This result will be at a cost of decreasing the H field intensity due to the increased impedance of the longer magnetic circuit in open air.

BRIEF DESCRIPTION OF THE DRAWINGS

FIG. 3 shows a cross-sectional view of a toroid showing one construction for accomplishing the peripheral tuning capacitance with an air gap between the two distributed asymmetric electrodes;

FIG. 4 shows a cross-sectional view of a toroid showing one construction for accomplishing the peripheral tuning capacitance with an air gap between two distributed symmetric electrodes;

FIG. 5 shows a cross-sectional view of a toroid showing another construction for accomplishing the peripheral tuning capacitance with a dielectric having a high dielectric constant filling the gap between the two distributed symmetric electrodes and a common third electrode;

FIG. 6 shows a cross-sectional view of a toroid showing another, construction for accomplishing peripheral tuning with air filling the gap between the two distributed symmetric electrodes and a common third electrode;

FIG. 11 discloses a square toroidal resonator cross section configuration which can be used in the invention;

FIG. 12 discloses a rectangular toroidal resonator cross section configuration which can be used in the invention;

FIG. 13 discloses yet another rectangular toroidal resonator configuration which can be used in the invention;

FIG. 14 discloses a circular toroidal resonator cross section configuration which can be used in the invention;

FIG. 15 discloses an oval type toroidal resonator cross section configuration which can be used in the invention;

FIG. 16 discloses a semi-circular toroidal resonator configuration which can be used in the invention;

FIG. 17 discloses a clover-leaf toroidal resonator cross section configuration which can be used in the invention;

DETAILED DESCRIPTION OF THE DRAWINGS

Figure 1:
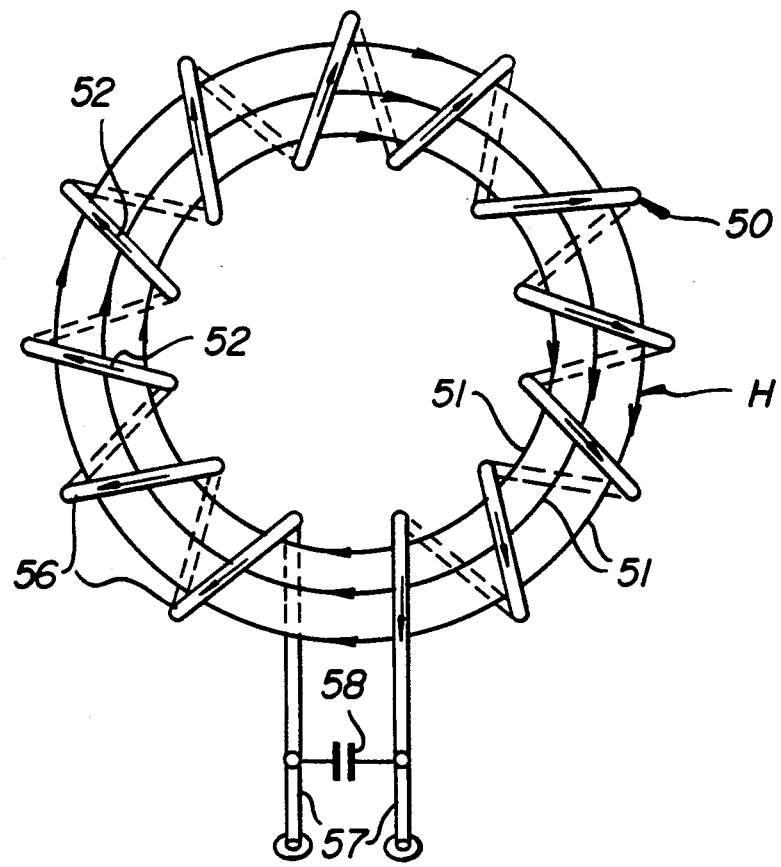
FIG. 1 is a top view of a lower frequency embodiment of the toroidal resonators on which the applicators according to the present invention are based.
Figure 2:
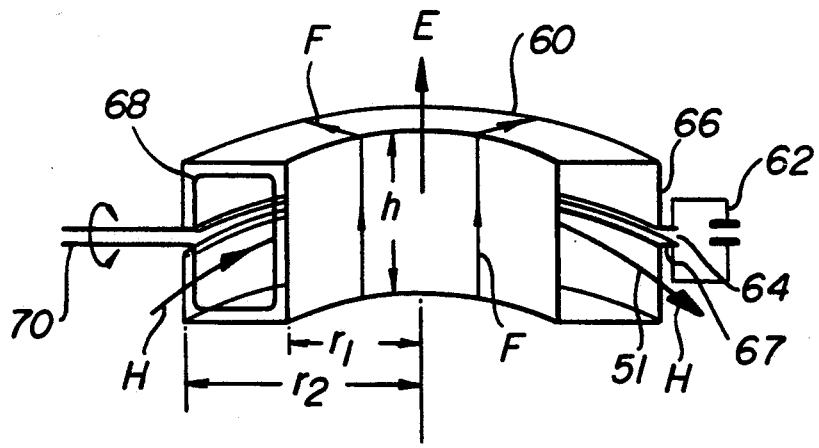
FIG. 2 is a perspective view with a half section cut away of a higher frequency embodiment of the toroidal resonator.

The preferred embodiment and best mode of the invention is shown by FIGS. 1, 2, and 4. The production of a confined RF magnetic field for therapeutic purposes may be described with the help of FIGS. 1 and 2, in which two embodiments of the basic electromagnetic (EM) structure of an OMTR device are present. In FIG. 1, the RF magnetic field H produced inside a low RF frequency toroidal resonator 50 by the RF current 52 flowing radially in the multi-turn wire winding 56 of the toroidal shaped resonator 50 (hereinafter referred to also as toroidal inductor) is represented by the uninterrupted H field line 51. This field is confined inside such a multi-turn winding conductive boundary. In order to obtain a high magnetic flux density, a high RF current intensity is needed. For this purpose, the tuning capacitance (C) 58 is connected to the terminals 57 of the toroidal inductor 50, the inductance (L) of which is calculated by standard textbook resonating at the frequency given by the well known equation $f=1/[2\pi\sqrt{LC}]$.

Figure 7A:
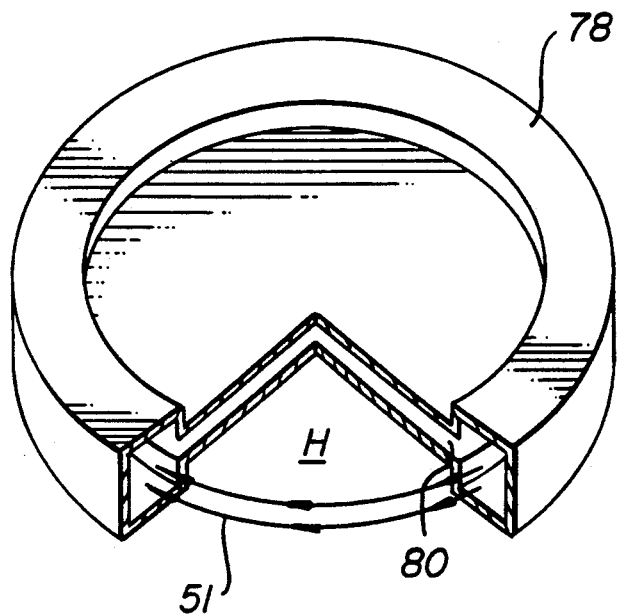
FIG. 7A is a perspective view with a section cut away of an embodiment of a toroidal resonator according to the present invention, in which the peripheral tuning capacitance is symmetrically distributed on the inner peripheral wall.

At higher frequencies, smaller L values are required, and the toroidal inductor consists simply of a single and distributed radial loop made of a folded conductive sheet conformed to the toroidal shape as in FIG. 2, where the rectangular cross section single loop torus 60 is shown with half a section cut away. An adequate number of tuning lumped capacitors 62 are uniformly connected along circumferential slot 64 on the external torus peripheral wall 66. In the fundamental resonating mode, the RF current lines are radial and flow as indicated by arrows F, and generate the EM field composed of the perpendicular E (electrical) and H (magnetic) fields. The E field distribution in the open space is dipolar; its axial direction is shown by arrow E. The torus H field lines 51 are always closed path lines traveling circularly inside the conductive wall, as shown by the illustrated representative field lines 51. This high RF frequency torus may be analyzed with the aid of the radial transmission line theory (see S. Ramo et al., Fields and Waves, J. Wiley & Sons, 1965), since the torus may be considered a distributed radial transmission line of axial symmetry, electrically short circuited at either the inner peripheral end as in FIG. 2, or at the external peripheral end as in FIG. 7, by a conductive wall. The electrical length of the radial line of FIG. 2 is always: $r_2-r_1-$, and, in most practical cases, is always: $r_2-r_1 << \lambda/4$, where $\lambda$ is the wavelength at the frequency of interest, and $r_1$ and $r_2$ are the internal and external radius of the torus, respectively. Under this condition, the impedance presented by the line at the external peripheral terminals 67 is inductive, with the inductance given by the approximate formula $L=(\mu_0 h/2)\ln(r_2/r_1)$ for the rectangular cross section torus of FIG. 2, where h is the torus height and $\mu_0$ is the free space magnetic permeability. FIG. 2 shows the toroidal resonator 60 excited by the RF energy supplied through the coupling loop 68. The RF energy from the RF source is delivered to the torus via the RF feed-line 70, which is terminated by the loop 68, which couples to the magnetic flux tube according to the angle formed with the flux line 51. This angle is adjusted by a rotatable joint until the reflected power is at the minimum. Although not shown in the drawings but well known to those skilled in the art, the rotation of the coupling loop can be set to a null point for the best matching also by an automatic servo mechanism.

In FIGS. 3 through 6, embodiments of capacitive tuning techniques alternative to the lumped capacitors 62 of FIG. 2 are shown. The distributed capacitance 72 is implemented by folding the edges of the peripheral conductive wall to constitute two facing electrodes in an asymmetric fashion as in FIG. 3, or in a symmetric fashion, as in FIG. 4. At higher frequencies, a smaller capacitance is required, and a third common electrode 74, which may be electrically grounded for added safety, is employed as in FIGS. 5 and 6 facing the two slot edges. The dielectric between the capacitance electrodes can be either air, as in FIGS. 3, 4 and 6, or a dielectric material 76 as in FIG. 5. The advantage in using a dielectric substance as a spacer is that it gives added structural support. Glass reinforced copper clad plastic of the type used in printed circuit boards is ideal at low RF frequencies. In addition, using a copper clad dielectric allows the space to be sealed shut making the toroid suitable as an air duct to carry refrigerated air used to cool the skin. This therefore is the preferred embodiment. In still another embodiment illustrated by FIG. 7A, a high RF frequency torus 78 exhibits its radial loop terminals along the inner peripheral conductive wall. The tuning capacitance 80 is manufactured with a single planar condenser, the two facing conductor plates of which are connected all around the circumferential edges and extend along the central space. The high Q factor torus 78 produces no stray electromagnetic field in the open space, exhibits high mechanical strength and is easily manufactured.

Figure 7B:
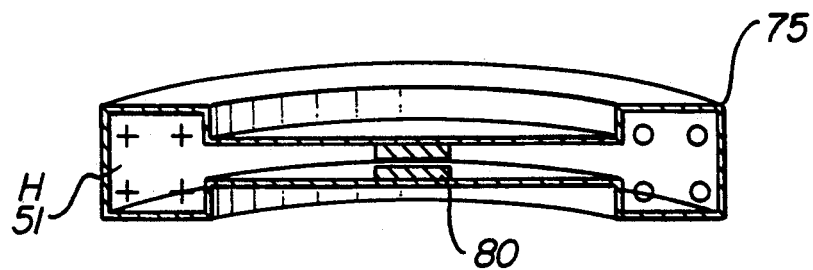
FIG. 7B is the cross section of a toroidal resonator showing a construction for accomplishing a symmetric lumped capacitive tuning.
Figure 7C:
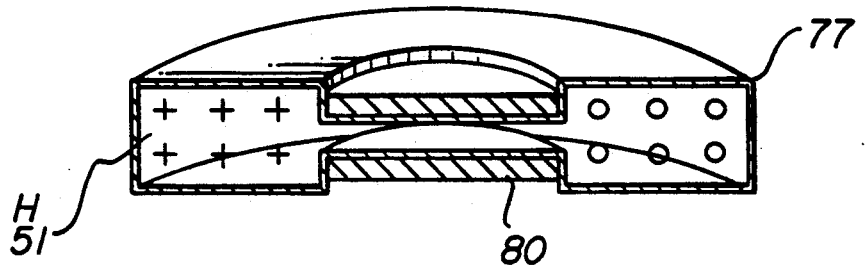
FIG. 7C is the cross section of a toroidal resonator showing another construction for accomplishing a larger torus inductance and a symmetric lumped capacitive tuning.

A lower frequency torus may be obtained by either increasing the inductance of the toroidal shape or the value of the tuning capacitance, or both. Two such embodiments are illustrated in FIGS. 7B and 7C. In 7B, the torus 75 is tuned by the variable lumped capacitor 80, which is added to the plate capacitance right at the center of the torus. In FIG. 7C, the higher inductance torus 77 is tuned by the variable lumped condenser 80 connected at the center of symmetry of the torus. The resonators 75, 77 and 78 of FIG. 7 may be described also as toroidal resonant cavities, which are resonating in their fundamental mode with the H field 51 following the same circular pathway as for the radial line resonators.

Figure 8:
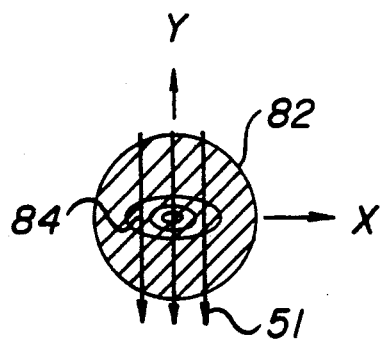
FIG. 8 is a top plan view of a cylindrical phantom having impedance and other electromagnetic characteristics of human tissue showing magnetic field lines and induced electric field loops.
Figure 9:
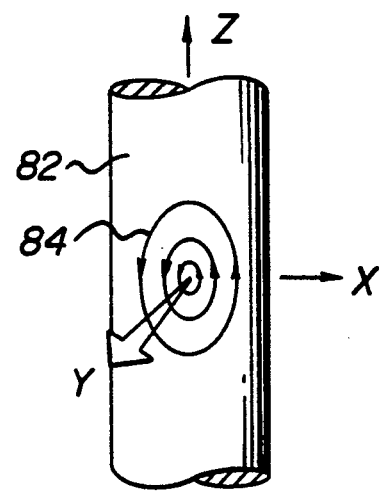
FIG. 9 is a side elevation view of a cylindrical phantom having impedance and other electromagnetic characteristics of human tissue showing electric field loops.
Figure 10:
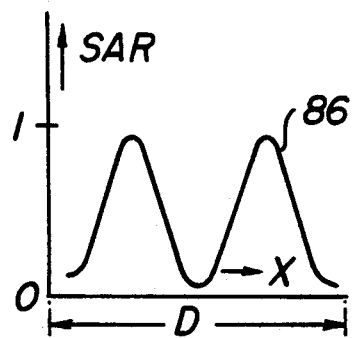
FIG. 10 is a double-bell curve graph showing normalized SAR distribution along the central x-axis of the cylindrical phantom shown in FIGS. 8 and 9.

The basic applicator according to the present invention is an Open Mode Toroidal shaped Resonator (OMTR), obtained from a toroidal resonator in which suitable apertures have been made in its conductive wall so that all or a part of the RF magnetic field of the toroidal resonator is made available for clinical use. OMTR applicators need to be developed to cope with clinical situations presenting largely variable requirements as far as magnetic field cross section shape and size and orientation with respect to the anatomy of the body part encompassing the tumor. This in turn requires OMTR devices of flexible design as regards to the aperture shape and size and the magnetic field configuration. Any proposed adjustment of the therapeutic field cross section shape and size and of the pathway of an OMTR device applicator and any proposed optimization of that applicator-body configuration for a given specific application will appear clear from a discussion of typical results on some typical heating patterns obtained by the magnetic field distribution of OMTR applicators. In FIGS. 8 and 9, the top view ([x,y] plane) and side view ([x,z] plane) of cylindrical phantom 82 having impedance and other electromagnetic characteristics of human tissue, is respectively shown. In FIG. 8 the magnetic field lines 51 flow through phantom 82 inducing the electric field loops 84, and associated induced eddy currents, producing therapeutic heat in the phantom conductive tissue. The inducing magnetic H field is directed along the phantom y-axis, while the induced current loops 84 lay along the perpendicular meridian [x,z] planes. The induced electric field pattern in FIG. 9 displays that the associated heat deposition pattern is approximately circumscribed to the cross section area of the magnetic field distribution in the [x,z] plane, with an intensity gradient towards the center of the loop, where the deposited power is zero. These results are typical of induced low frequency RF eddy currents in Microwave Theory and Techniques, Vol.MTT-34, pp.612-619, 1986). In FIG. 10, a typical normalized SAR distribution 86 along the central axis of cylindrical phantom 82 is shown for the heating arrangement of FIGS. 8 and 9. The SAR distribution 86 takes the shape of a double-bell curve, zero valued at the phantom center in correspondence with the zero electric field value, and smaller valued also at the superficial fat layer, which has much lower conductivity. Therefore, either one of the maxima of the RF heating current pattern is useful for heating tumor masses at depth without overheating the superficial tissues.

Preferred embodiments for obtaining the above mentioned OMTR design flexibility are the following:

In FIGS. 11-17 examples of various geometrical OMTR conductive wall cross-section shapes are shown which help to shape the magnetic field cross section, and therefore the heating field cross section. They are: square (FIG. 11), rectangular (FIGS. 12, 13), circular (FIG. 14), ellipsoidal (FIG. 15), triangular (FIG. 16) and stellar (FIG. 17). Other shapes, also irregular, may be embodied according to the clinical needs. For some of these cross section geometrical shapes, textbook formulae are available for calculating the radial line inductance, and in these cases the tuning capacitance is determined a priori. In remaining cases, the tuning capacitance has to be determined experimentally.

Figure 18:
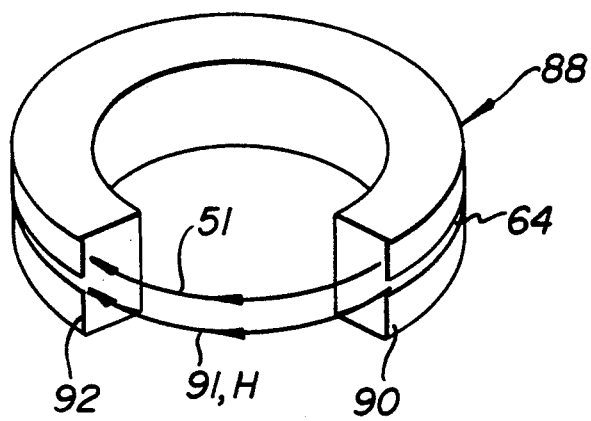
FIG. 18 is a perspective view of the embodiment of a higher frequency RF applicator according to the present invention which is exhibiting a rectangular cross section and in which the treatment ports for obtaining the therapeutic field are totally interrupting the conductive wall of the applicator and are cut along radial cross sections.
Figure 19:
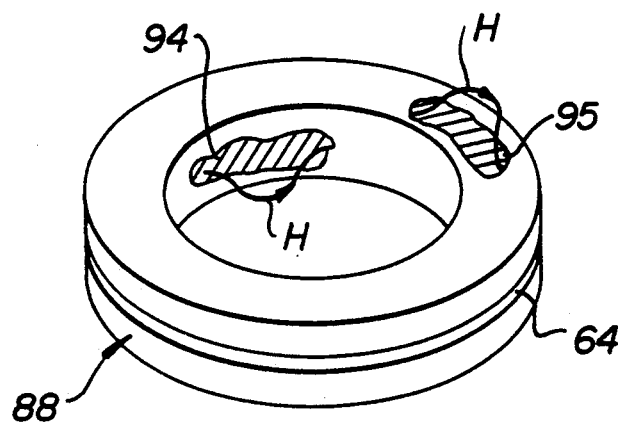
FIG. 19 is a perspective view with parts cut away of an alternative embodiment of side apertures on the conductive wall of an applicator according to the present invention.
Figure 20:
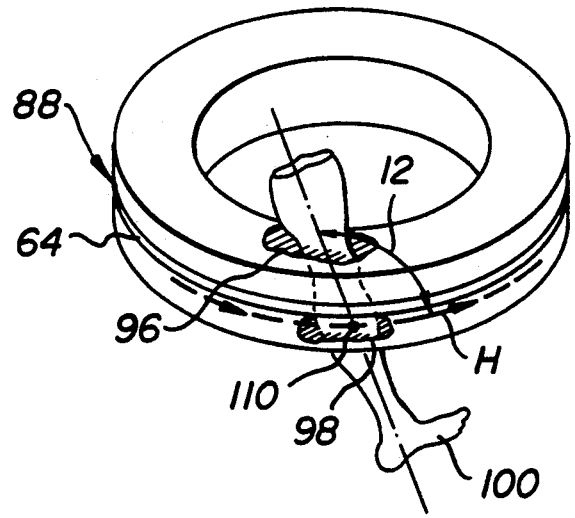
FIG. 20 is a perspective view with parts cut away of an alternative embodiment of side apertures on the conductive wall of an applicator according to the present invention which allow an extended body part to be inserted into a hollow cavity wall of the torus.

In FIG. 18, the OMTR 88 is obtained by cutting away a radial segment to a toroidal resonator to generate the rectangular cross section terminal apertures 90 and 92. The magnetic field useful for therapeutic purposes, i.e., the therapeutic field, is represented by the field lines 51, and is available in the open space flowing uninterrupted through the OMTR and the air gap 91 between apertures 90 and 92. This air gap shows the extent of the OMTR useful space into which the portion of the body under treatment can be inserted. A high RF frequency toroidal resonator prototype working at 27 MHz has been developed and exhibits the following dimensions: $r_1 = 13.5$ cm, $r_2 = 24$ cm, and $h = 10$ cm, while a prototype working at 93 MHz exhibited the following dimensions: $r_1 = 13.5$ cm, $r_2 = 24$ cm, and $h = 10$ cm. Only a slight decrease is observed in the resonance frequency and in the quality factor is observed when a radial segment of 1/6 of the circumferential length of the conductive wall of these toroidal prototypes is removed. It is seen that both OMTR prototypes exhibit a therapeutic field distribution of cross section size and air gap useful for clinical applications FIGS. 19 and 20 show views of alternative embodiments of OMTR applicators, in which the apertures for obtaining the therapeutic field are cut along the side conductive walls of the torus, without interrupting totally the conductive wall. FIG. 19 shows examples of how a single side aperture 94 and top aperture 95 of any shape and size may be made on selected points of the conductive wall of the OMTR 88 to make available a portion of field H in the open space for the treatment of superficial or subcutaneous tumors which may easily be exposed to apertures of this type. FIG. 20 is a view of OMTR 88 on the conductive wall of which a pair of apertures 96 and 98 have been made which allow an extended body part, such as a limb 100, to be inserted into a hollow cavity wall of the torus to be surrounded by the therapeutic field H for treatment of tumor 110. By giving a suitable offset to apertures 96 and 98, the field H is incident to the tumor with any value of angle 112. The protrusion of an extremity through the torus is rarely necessary since the part can be positioned in the normal gap used for treatment. It is shown for the sake of comparison.

The following embodiments are examples of means for the adjustment for the cross section shape and size of the pathway of an OMTR applicator and for the optimization of the applicator-body configuration for specific clinical situations.

Given the radial flow pattern of the RF currents in the basic resonators, these may be developed other than in a single piece, by assembling a plurality of toroidal segments individually resonating at the same frequency, and aligned in a multi-element closed chain, forming any pattern, the most simple being circular, with contiguous segments close to each other to allow effectual magnetic coupling and the propagation of the uninterrupted magnetic field lines along the toroidal resonant segment chain. The mechanical connection holding the segments together need to be done neither with magnetic material nor with conductive material, and can be made of any dielectric material (plastics, etc.).

Figure 21:
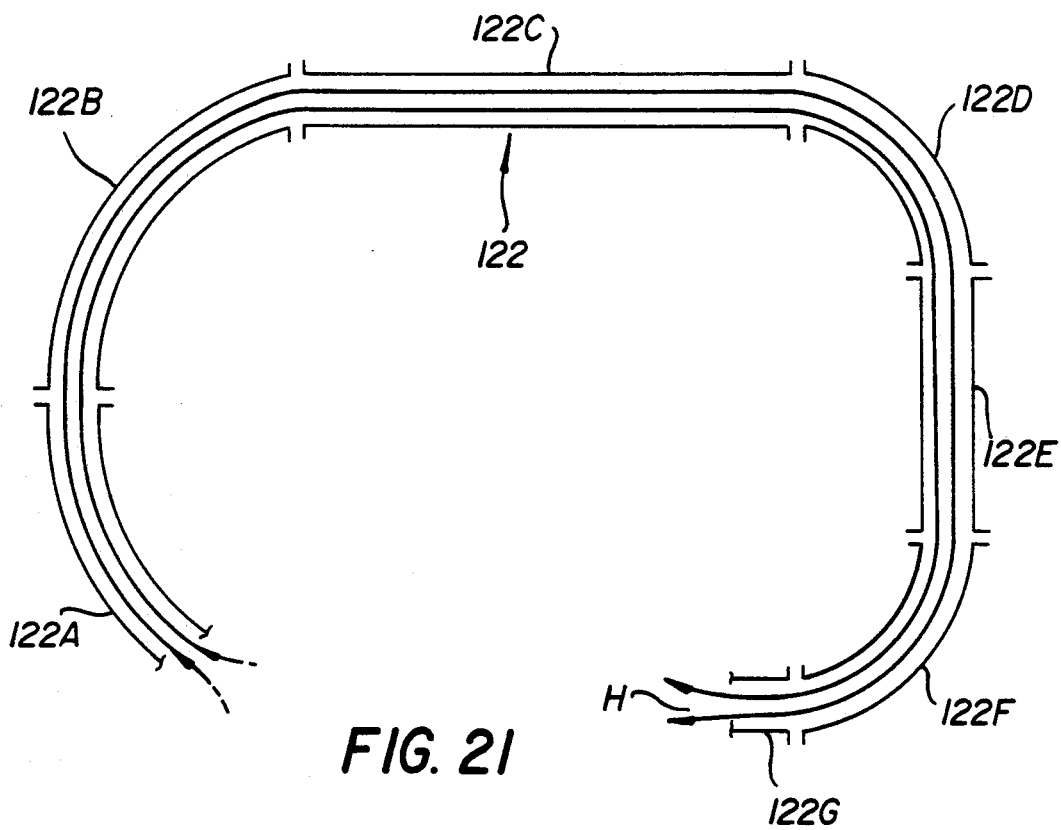
FIG. 21 is a schematic representation of the top view of an alternate embodiment of a flexible toroid applicator.

FIG. 21 is a top view with parts cut away of embodiments of the specific magnetic pathway of a multi-element OMTR applicator 122, showing seven OMTR segments from 122(a) to (g), which are independently resonating at the same RF frequency, and are aligned to form a chain of continuous segments connected to couple magnetically the uninterrupted magnetic field lines H. At lower RF frequencies, resonant OMTR segments constituted by independent and resonant winding segments are mechanically coupled together by similar means to form a similar uninterrupted magnetic pathway.

Figure 22:
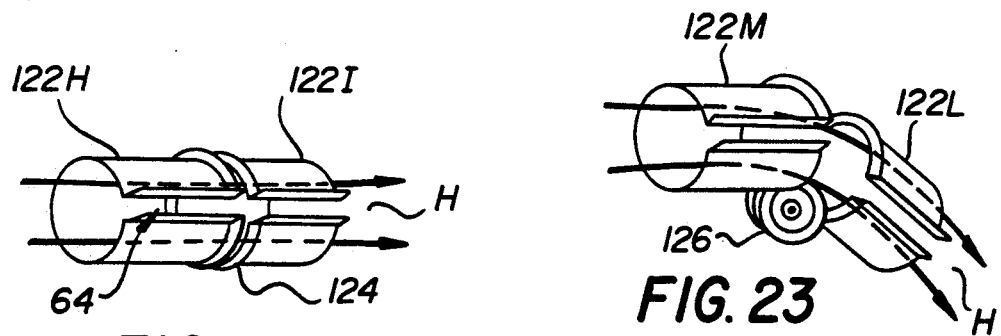
FIG. 22 is a view of two segments of the toroid applicator mechanically coupled by their joint flanges and showing the flux flow.
Figure 23:
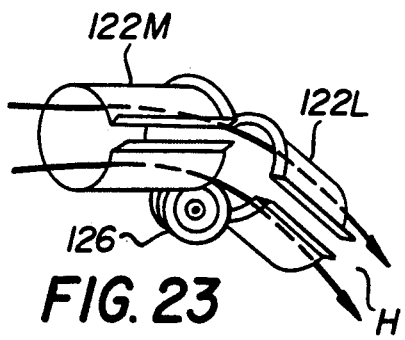
FIG. 23 is a view of FIG. 22 showing hinged sections which are open to show flux flow.

In FIGS. 22 and 23 alternative embodiments of mechanical joints connecting contiguous high frequency OMTR segments are shown. In FIG. 22 the OMTR segments 122(h) and 122(i) are mechanically connected by the rigid flange pair 124. In FIG. 23 the OMTR resonating segments 122(l) and 122(m) are mechanically connected by hinge 126.

Figure 24:
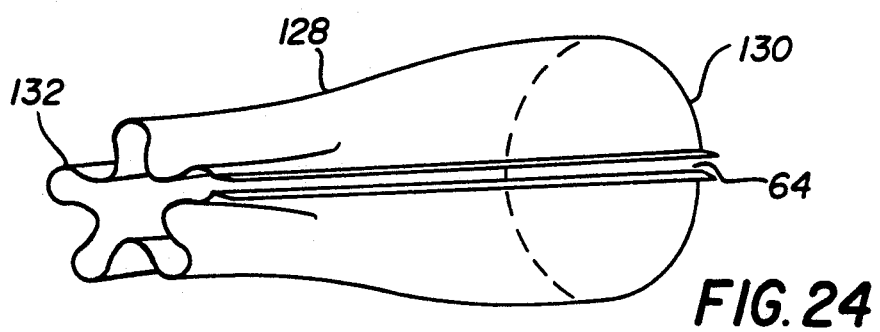
FIG. 24 is a perspective sectional view of a toroidal resonator segment showing the transition between a circular cross section of FIG. 14 and the stellar type of cross section of FIG. 17.
Figure 25:
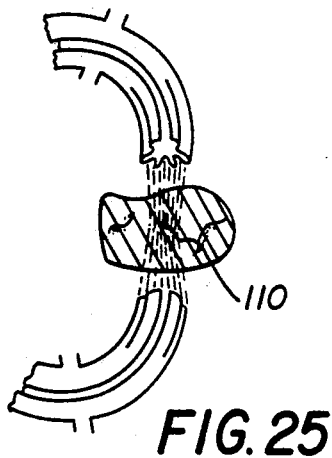
FIG. 25 represents a schematic showing the flux flow through a tumor in which the tumor is approached by the treatment ports anteriorly and posteriorly.
Figure 26:
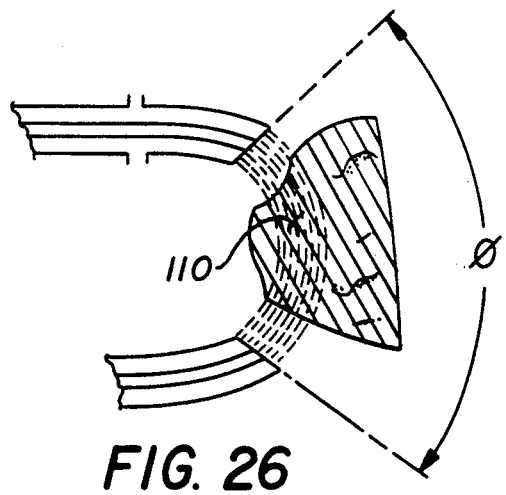
FIG. 26 represents a schematic showing the flux flow through a tumor in which the treatment ports are not tangential but angular towards one another.
Figure 27:
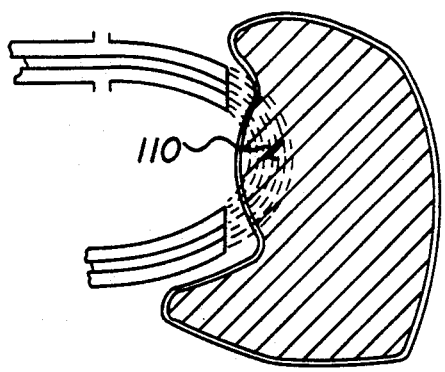
FIG. 27 represents a schematic showing the flux flow through a tumor in which the tumor is approached by the treatment ports for tangential treatment.
Figure 29:
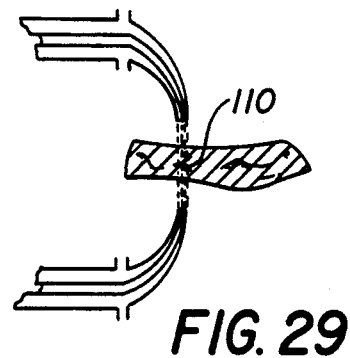
FIG. 29 represents a schematic showing the flux flow through a tumor in which both treatment ports have small apertures to concentrate the heat.
Figure 30:
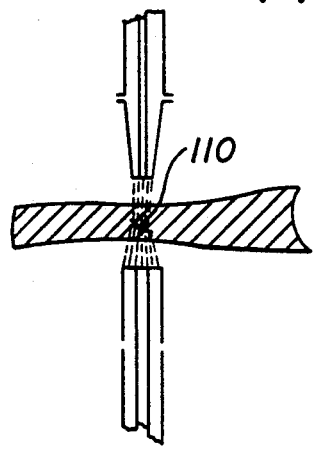
FIG. 30 represents a schematic showing the flux flow through a tumor in which the field is shaped three dimensionally with one treatment port having a larger aperture than the other port.
Figure 28:
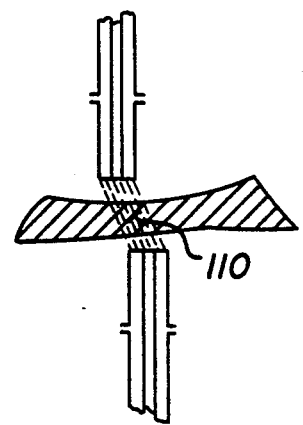
FIG. 28 represents a schematic showing the flux flow through a tumor where the treatment ports are offset from one another to direct the flux tube at an angle over the tumor, the tumor still remains under constant heating.

In FIG. 24 an embodiment of the high frequency transition OMTR segment 128 is shown exhibiting cross section terminal apertures 130 and 132 of different shape and size, the segment 128 is independently tuned by capacitors of proper value connected at the slot 64. Lower frequency transition OMTR segments are implemented by simply changing the cross section shape and size of the multi-turn winding mandrel. Transition toroidal resonator segments may be used to provide treatment ports of suitable terminal cross section shape and size by changing the cross section shape and size as shown in FIG. 29 of an existing OMTR. In an OMTR applicator exhibiting a radial aperture gap of a flexible magnetic field pathway, the tumor 110 being treated need not be approached only anteriorly and posteriorly as is shown in FIG. 25, which is ideal for deep tumors. Instead, the tumor can also be treated tangentially. This is ideal for superficial tumors. These tumors occur in a large variety of anatomical sites, and examples of adequate OMTR pathways and treatment port configurations are shown in FIGS. 26 and 27. In FIG. 26 the angle between treatment port planes is smaller than 180°, which is useful when it is desired to miss a deep structure such as the bone when treating the thigh. In FIG. 27 the treatment ports are close and shaped to treat the superficial tumor sitting at the bottom of a cavity. Also, the treatment ports can be offset from one another as in FIG. 28 in order to change the incidence angle of the therapeutic field. This configuration is especially useful for changing the angle of incidence of the field, yet keeping the tumor under constant heating. The treatment ports may be made very small by the use of transition OMTR segments so as to concentrate the heat in a small cross section employing two end transitional toroidal resonator segments as in FIG. 29. Also, the therapeutic field may be shaped longitudinally by making one treatment port of larger cross section than the other, as in FIG. 30. It may be seen that a large variety of therapeutic field beams may be generated for treatment optimization by adjusting the shape, size, and configuration of these treatment ports. Thus, the versatility of the entire apparatus can be appreciated. The sophistication of heating patterns and volumes is unique to the field of hyperthermia.

A number of methods may be implemented to enhance either the already confined heating of an OMTR applicator over the target volume with added safety.

Figure 31:
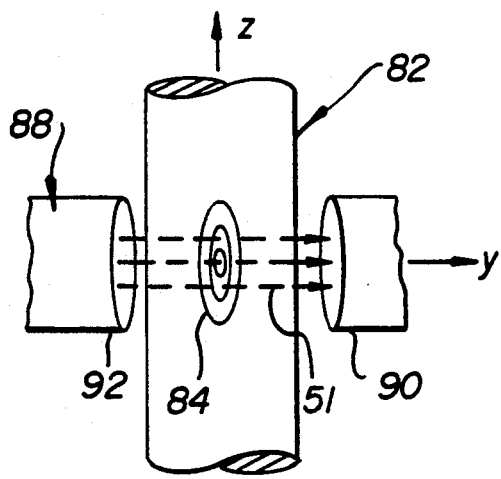
FIG. 31 is a side elevation view of treatment ports of the OMTR aimed at the phantom and the therapeutic magnetic field.
Figure 32:
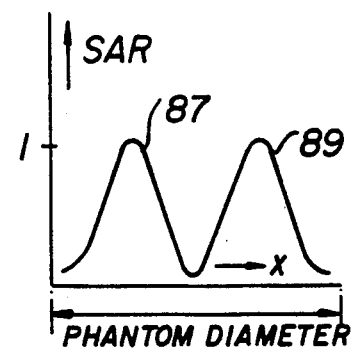
FIG. 32 is a graph of FIG. 31 showing a double bell SAR distribution.
Figure 33:
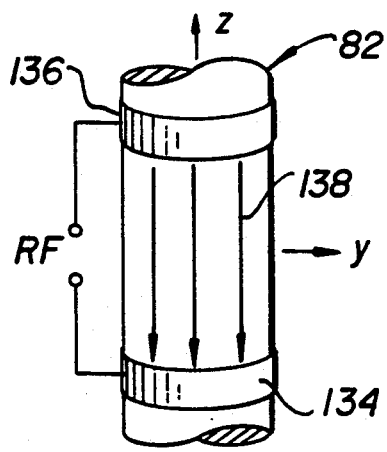
FIG. 33 is a side elevation view with two capactive electrodes wrapped around the same phantom.
Figure 34:
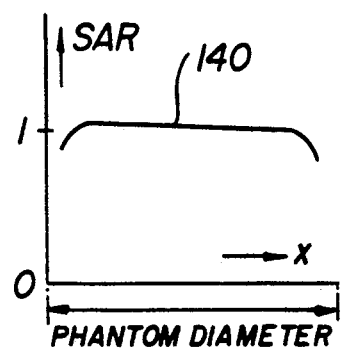
FIG. 34 is a graph of FIG. 33 showing SAR distribution if measured along the central diameter along the x-axis.
Figure 35:
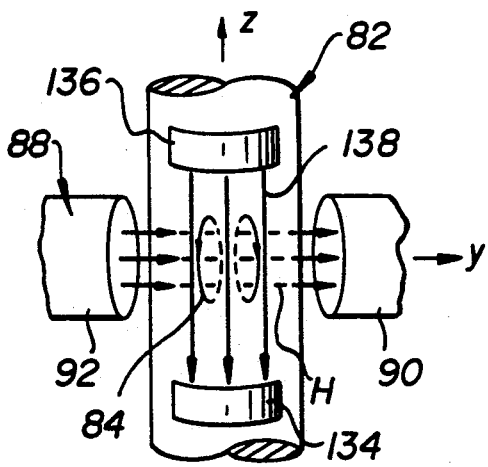
FIG. 35 is a side elevation composite of FIGS. 31 and 33 in which the OMTR and the capacitive heating device are both connected to the same body part.
Figure 36:
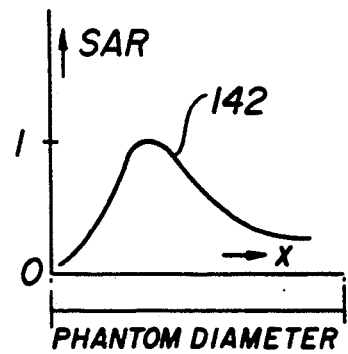
FIG. 36 is a graph of FIG. 35 showing SAR distribution and exhibiting a single broad maximum of variable depth and intensity according to the relative intensities of the superimposed coherent fields and their phase relationships.

Additional EM fields may be superimposed to the EM heating field of an OMTR applicator, to give rise to a substantially constructive interface effect, preferably over the target volume, to provide safely a locally enhanced temperature rise. In FIG. 31 a side view ([y,z] plane) is shown of the treatment ports 90 and 92 of OMTR 88 that are aimed at the phantom 82, and the therapeutic magnetic field 51 induce the E field loops 84 in the conductive tissue, giving rise to the double bell SAR distribution 87 and 89 of FIG. 32, when measured along the central phantom diameter along the x-axis, which is perpendicular to the plane of the drawing. It appears also that the maxima of curves 87 and 89 are relative to fields, that in central cross section plane exhibit opposite phase, since they are generated by closed field loops crossing such a plane. In FIG. 33 the same [y,z] view shows the auxiliary applicator consisting of two capacitive electrodes 134 and 136 wrapped around the same phantom 82, and giving rise directly to the axial electric field distribution 138 and to the SAR distribution 140 of FIG. 34, when measured along the same central diameter along the x-axis. This distribution result is almost uniform in the phantom cross section and exhibits the same phase across any phantom cross section. If the two applicators 88 and 134 are both connected to the same phantom and energized simultaneously by coherent RF energy, an SAR distribution as shown in FIG. 35 is obtained. This exhibits a single broad maximum of variable depth and intensity according to the relative intensities of the two superimposed fields and to their phase relationships. In fact, in nearly half the phantom cross sections, the superimposed RF field distributions corresponding to the SAR patterns 87 and 140 of the two applicators may be generated having the same phase and therefore interfere positively producing enhanced heating. In the other half phantom cross section, the superimposed RF field distributions corresponding to the SAR patterns 89 and 140, have instead opposite phase and therefore interfere negatively and no maximum occurs. This method possesses a further advantage in that each heating device is energized with nearly half of the RF power needed for obtaining comparable results by a single applicator. Therefore, the proposed treatment is safer since the access tissues below each single device are more likely to be spared from overheating.

Such additional RF fields may be generated by auxiliary circuits energized by external power sources that are phase coherent with that of the OMTR field. Alternatively, the auxiliary fields may be obtained by suitable magnetic coupling of the auxiliary circuit to the OMTR field. At low RF frequencies these auxiliary circuits are administered by capacitive electrodes, inductive coils, and hybrid combinations of these, that give rise to RF heating currents which are flowing across the tissue. At higher RF frequencies, these devices include wave guide apertures, dipoles, and other antennae which are predominantly radiating electromagnetic energy over tissue. In all of these cases, the relative intensity and phase of all of the interfering fields may be controlled on the various portions of the tissue in order to give rise to the wanted constructive interference effect only over the tumor volume, with means well known to people expert in electromagnetism.

By mechanical means incorporated in the apparatus, motion can be imparted to the OMTR so as to scan the tumor (as in U.S. Pat. No. 4,230,129 of one of the inventors), and in other specified ways so that the energy can be distributed over a wide skin area as shown by FIGS. 37–42. The therapeutic field may be kept collimated over the deep tumor target by a suitable selection of OMTR cross section, aperture conformation, and scan path so that the cancer is continuously subject to the heating field, and its internal temperature can be raised to any selected temperature, for example, to 45° C., while the overheating of the tissue in the access pathway is avoided, since heating of this tissue is only intermittent.

Figure 37:
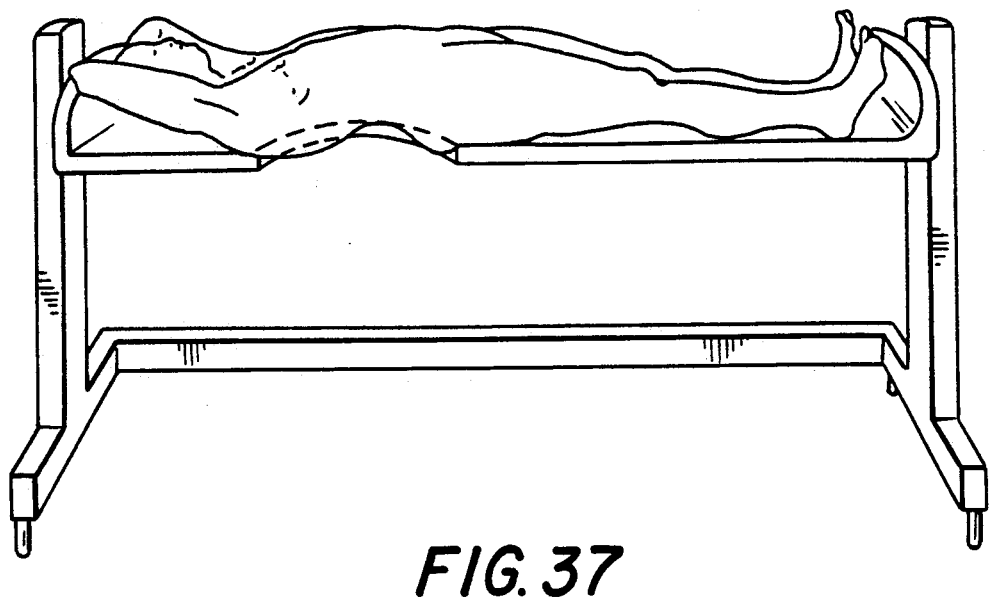
FIG. 37 is a perspective view of a patient lying on a cutout in a table to expose the chest anteriorly and posteriorly to enable lung cancer to be treated.
Figure 38:
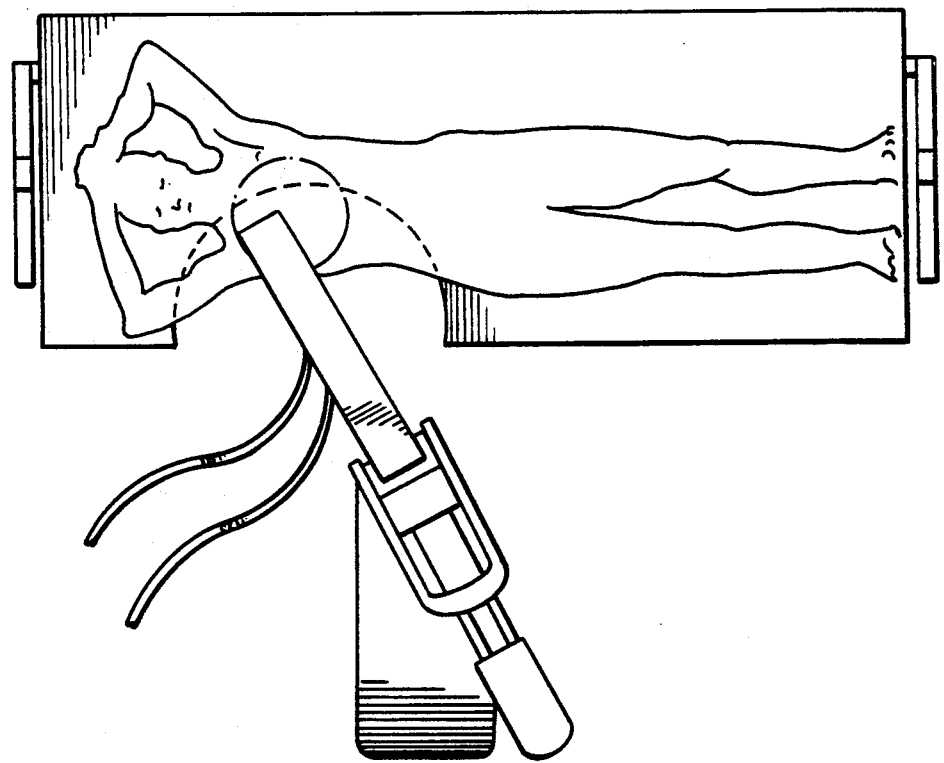
FIG. 38 is a perspective view of the patient of FIG. 37 with the radio frequency applicator moved in against the patient with movement motions of the aperture of the toroid being shown as dotted lines.
Figure 39:
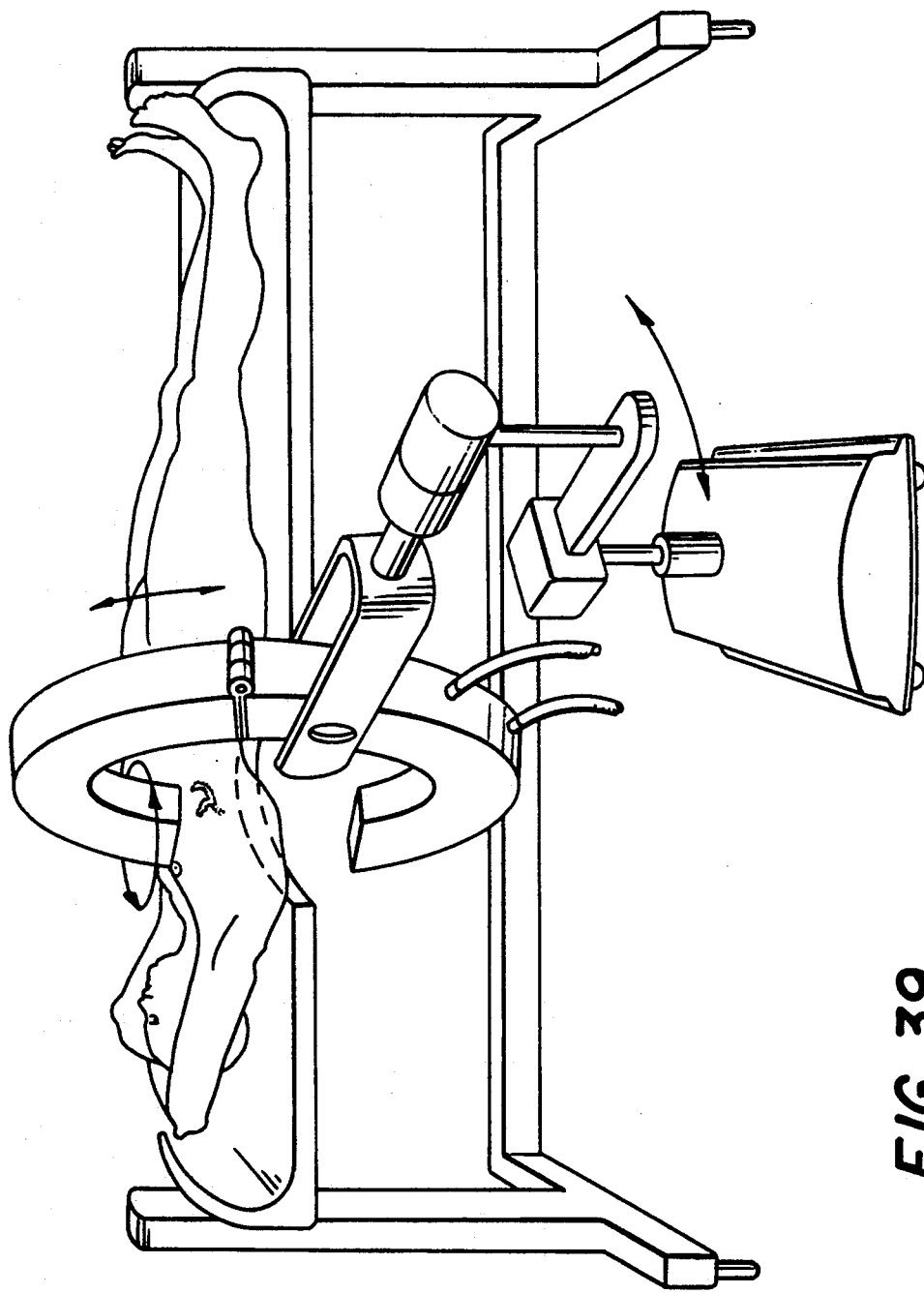
FIG. 39 is a perspective view with parts cut away of an alternative embodiment of the system of FIG. 37 and 38 in which the actuator is computer controlled.
Figure 40:
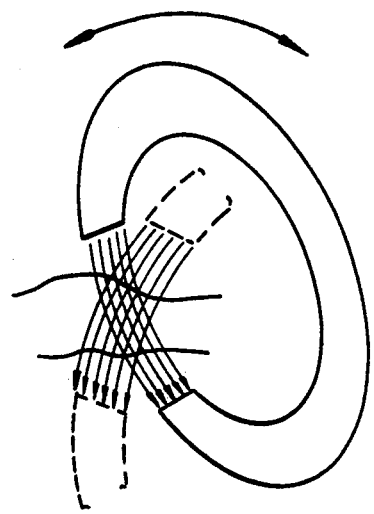
FIG. 40 is a schematic representation showing the motion of the toroid aperture in a rocking mode.
Figure 41:
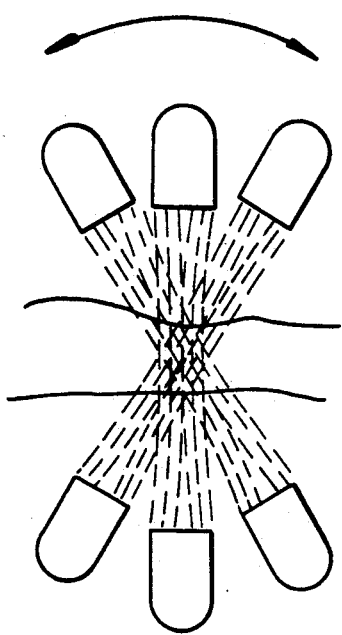
FIG. 41 is a schematic representation showing the motion of the toroid aperture in a swiveling mode.

In FIGS. 37 and 38 perspective views with parts cut away of an alternative embodiment of a hyperthermia method employing an OMTR applicator provided with mechanical scanning means are shown. The patient to be treated usually lies on a non-conductive table with the part to be treated exposed both anteriorly and posteriorly. This is best accomplished by a cut out wooden or a plastic table. In FIG. 37 the patient is lying on a cutout in table to expose the chest anteriorly and posteriorly to enable lung cancer to be treated. In FIG. 38 the heating apparatus has been moved in and possible motions of the treatment ports of the OMTR applicator are shown as dotted lines. The smaller circular motions of the OMTR applicator could be traced and the larger arc covered to complete heating the entire section. Usually, the small arc is centered over the tumor and rotated for the width of the heated segment.

Figure 42:
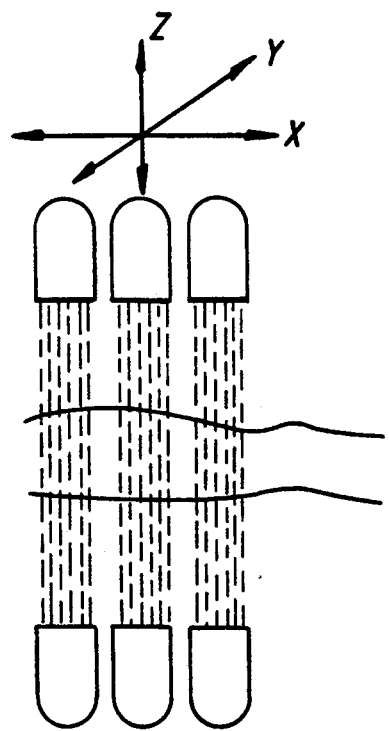
FIG. 42 is a schematic with parts cut away of alternative embodiments of the system in FIGS. 37 and 38 in which the RF applicator according to the present invention is moved by translating movements to generate any complex energy pattern.

FIG. 38 shows a simple small circular motion around a lung tumor. Although, this is a possible motion for the therapeutic head, a computer controlled actuator can make any simple compound or complex movement in three directions, as in FIG. 39. The torus could rock back and forth as in FIG. 40, or could swivel back and forth as in FIG. 41, while collimating on the tumor. Moreover, the OMTR can easily be translated in space along any x,y, and z direction as shown in FIG. 42. In addition, although not shown in the figures, the angle at which the heating magnetic field is collimated on the tumor may be averaged over a range of values by staggering motion of the OMTR ports of a flexible OMTR, as shown by the example in FIG. 28. Swivelling, rocking, and translating motions could be combined in any complex pattern to focus the EM energy on the tumor while moving conformably to any complex anatomic surface.

As alternative to a single large cross section OMTR working at lower RF frequency, and with the purpose of producing a large area of heating of specific shape and size, a multiple OMTR applicator may be implemented assembling a multiplicity of independent OMTR flux guides, working at the same or at different frequency.

It should be noted that the steps of the inventive process can be interchangeable without departing from the scope of the invention. Furthermore, these steps can be interchanged and are equivalent. In the foregoing description, the invention has been described with references to a particular preferred embodiment, although it is to be understood that the specific details may be carried out in other ways without departing from the true spirit and scope of the following details.

What we claim is:

1. An electromagnetic treatment method for confined heating of a tumor to therapeutic temperatures comprising the steps of:
   (a) producing a high density magnetic field confined within a conductive wall pathway of a toroidal resonator, said toroidal resonator being provided with adjustable coupling means for matching to a RF power source, the frequency of said source being comprised within the range from about 20 kHz to about 1000 MHz;
   (b) exposing a body part to one or more apertures in said conductive wall of said toroidal resonator, so that at least a part of said magnetic field is made available as a therapeutic field to be coupled magnetically to the body part encompassing the tumor;
   (c) adjusting said therapeutic field to specific size and shape and orientation to be coupled to said body part in order to produce confined heating of a specific tumor, said adjusting including changing the configuration and size of said toroidal resonator and said apertures; and
   (d) enhancing said confined heating and its tumoricidal effects.

2. An electromagnetic treatment method as claimed in claim 1 including the step of extending the treatment to large tumors exhibiting a cross section which is substantially larger than the cross section of said therapeutic field.

3. An electromagnetic treatment method as claimed in claim 2 wherein the step of extending the treatment to large tumors by said therapeutic field produces uniform heating throughout the tumor tissue.

4. An electromagnetic treatment method as claimed in claim 1 wherein said enhancing step of said confined heating of said tumor includes the step of controlling tumor blood perfusion rate during the treatment with said therapeutic field.

5. An electromagnetic treatment method as claimed in claim 4 wherein said controlling tumor blood perfusion rate includes means such as the temporary occlusion of the major blood vessels supplying the tumor, the occlusion and thrombosis of the major branches supplying the tumor, the embolism of the end blood supply and the reduction of the systemic blood pressure by vasodilation.

6. An electromagnetic treatment method as claimed in claim 1 wherein said enhancing step of said confined heating of said tumor includes depositing lossy ferromagnetic material in the bulk of said tumor mass.

7. An electromagnetic treatment method as claimed in claim 1 wherein said enhancing step of said confined heating of said tumor produced by said therapeutic field include the superposition over said tumor of additional auxiliary electromagnetic and non-electromagnetic heating fields generated by additional auxiliary heating devices.

8. An electromagnetic treatment method as claimed in claim 1 wherein said enhancing step of said confined heating of said tumor include the superposition to said therapeutic field of additional auxiliary heating fields generated by additional auxiliary electromagnetic heating devices, said auxiliary fields being directed over said tumor and coherent with said therapeutic field and controlled in phase, amplitude and orientation to give a rise to a positive interference pattern with said therapeutic field over said tumor.

9. An electromagnetic treatment method as claimed in claim 8 in which said additional auxiliary electromagnetic devices generating said coherent auxiliary fields are energized by a direct electromagnetic coupling with said therapeutic electromagnetic field.

10. An electromagnetic treatment method as claimed in claim 1 wherein said enhancing step of said therapeutic effect of said confined heating of the tumor includes the administering of either thermosensitizing or tumoricidal drugs.

11. An apparatus for electromagnetic hyperthermia heating of a tumor located in a body to therapeutic temperatures comprising:
   a toroidal resonator assembly with a conductive wall means defining a patterned power source, means for producing a high density magnetic field confined within said conductive wall means of said toridal resonator assembly forming a pathway, adjustable coupling means connected to said toroidal resonator assembly for matching an RF power source, the frequency of said source being comprised within a range from about 100 kHz to about 1000 MHz;
   said conductive wall means of said toroidal resonator assembly defining aperture means configured to receive a body part, wherein at least a part of said magnetic field is made available as a therapeutic field to be coupled magnetically to a body part encompassing the tumor and exposed to said aperture means;
   means for adjusting said therapeutic field to specific size and shape and orientation to be coupled to said body part in order to produce confined heating of said tumor, said field adjusting means including changing the cross section shape, size and wall means pathway of said toroidal resonator assembly and the shape, size and configuration of said aperture means.

12. An apparatus for electromagnetic hyperthermia heating of a tumor located in a body to therapeutic temperatures comprising:
   a toroidal resonator assembly with a conductive wall means of radial configuration defining a pathway and a patterned power source, means for producing a high density magnetic field confined within said conductive wall means, adjustable coupling means connected to said toroidal resonator assembly for matching an RF power source, the frequency of said source being comprised with a range from about 100 kHz to about 1000 KHz;
   said conductive wall means of said toroidal resonator assembly defining at least one aperture, wherein at least a part of said magnetic field is made available as a therapeutic field to be coupled magnetically to a body part encompassing the tumor and exposed to said at least one aperture;

means for adjusting said therapeutic field to specific size and shape and orientation to be coupled to said body part in order to produce confined heating of said tumor, said field adjusting means including changing the cross section shape, size and pathway of said toroidal resonator assembly and means for enhancing said confined heating and its tumoricidal effects.

13. A resonator for treatment of tumors at frequencies within the range from 1 MHz to about 1000 MHz, comprising toroidal resonator means formed of a folded conductive wall, the conductive wall of resonator means being configured to conform to a field pathway forming a magnetic fieldj with an external magnetic field portion being of a density as high as that within the toroidal resonator means, means for adjusting said magnetic field including changing said configuration of said conductive sheet to a variety of field pathways, said radial loop being formed with terminal edges defining a slot, said slot being aligned parallel to said field pathway, and provided with tuning capacitance means which include distributed and lumped capacitors uniformly connected along said slot.

14. A resonator as claimed in claim 13 wherein said means for adjusting said magnetic field comprises:

a cut out segment in said resonator means to totally interrupt said conductive wall of said resonator means with two cross section apertures at the extremities of said conductive wall, said interruption providing an air gap in which said body part is inserted, said means for adjusting said magnetic field including the shaping of said cross section apertures and of the configuration of said air gap.

15. A resonator as claimed in claim 13 wherein said resonator is toroidal and of suitable shape and size with said capacitance means being adjusted to bring it to resonance;

at least one transition resonant toroidal segment inserted in said toroidal resonator pathway, each said transition resonant segment being provided with capacitive tuning means and having terminal cross sections configured to match with the cross section of contiguous segments to provide strong magnetic coupling.

* * * * *